US007482331B1

(12) United States Patent
Bristow et al.

(10) Patent No.: US 7,482,331 B1
(45) Date of Patent: Jan. 27, 2009

(54) DIAGNOSIS AND TREATMENT OF MYOCARDIAL FAILURE

(75) Inventors: Michael R. Bristow, Greenwood Village, CO (US); Leslie A. Leinwand, Boulder, CO (US); Wayne Minobe, Golden, CO (US); Koichi Nakao, Kumamoto (JP)

(73) Assignee: The Regents of the University of Colorado, Boulder, CO (US)

( * ) Notice: Subject to any disclaimer, the term of this patent is extended or adjusted under 35 U.S.C. 154(b) by 1470 days.

(21) Appl. No.: 09/558,472

(22) Filed: Apr. 25, 2000

Related U.S. Application Data

(62) Division of application No. 09/016,075, filed on Jan. 30, 1998, now abandoned.

(60) Provisional application No. 60/038,911, filed on Feb. 26, 1997, provisional application No. 60/036,987, filed on Jan. 30, 1997.

(51) Int. Cl.
*A01N 43/04* (2006.01)
*C12N 15/63* (2006.01)
*C07H 21/04* (2006.01)

(52) U.S. Cl. .................. 514/44; 435/455; 536/23.5

(58) Field of Classification Search .............. 800/3, 800/8, 9, 13, 18; 514/44; 424/93.21; 435/325, 435/455; 536/23.5
See application file for complete search history.

(56) References Cited

U.S. PATENT DOCUMENTS

| 5,219,727 A | 6/1993 | Wang et al. ............... 435/6 |
| 5,476,774 A | 12/1995 | Wang et al. .............. 435/91.2 |
| 5,580,722 A | 12/1996 | Foulkes et al. ............. 435/6 |

FOREIGN PATENT DOCUMENTS

WO    WO 93/21339    10/1993

OTHER PUBLICATIONS

Eck et al. "Gene Based Therapy" in The Pharmacological Basis of Therapeutics, McGraw-Hill, 1996, pp. 77-101.*
Miller, N and R. Vile. "Targeted vectors for gene therapy," 1995, FASEB J., vol. 9, pp. 190-199.*
Deonarain, M. "Ligand-targeted receptor-mediated vectors for gene delivery," 1998, Expert Opin. Ther. Pat., vol. 8, pp. 53-69.*
Verma, I and N. Somia. "Gene Therapy—Promises, problems and prospects," Sep. 1997, Nature, vol. 389, pp. 239-242.*
Crystal, RG. "Transfer of genes to humans: Early lessons and obstacles to success," 1995, Science, vol. 270, pp. 405-410.*
Nabel, EG. "Gene Therapy for Cardiovascular Disease," Circulation, 1995;91: 541-548 (pp. 1-17).*
Hajjar, R. et al. "Prospects for Gene Therapy for Heart Failure," Circulation Research, 2000;86:616 (pp. 1-12).*
Alexander et al., "Gene transfer and models of gene therapy for the myocardium," *Clin. Exp. Pharmacol. Physiol.*, 26:661-668, 1999.

Arai et al., "Alterations in sarcoplasmic reticulum gene expression in human heart failure," *Circulation Research*, 72(2):463-469, 1993.
Boluyt et al., "Alterations in cardiac gene expression during the transition from stable hypertrophy to heart failure," *Circ. Res.*, 75:23-32, 1994.
Bouvagnet et al., "Distribution pattern of α and β myosin in normal and diseased human ventricular myocardium," *Basic Res. Cardiol.*, 84:91-102, 1989.
Bristow et al., "Reduced β1 receptor messanger RNA abundance in the failing human heart," *Clin. Invest.*, 92:2737-2745, 1993.
Calovini et al., "Steroid-hormone regulation of myosin subunit expression in smooth and cardiac muscle," *Journal of Cellular Biology*, 59:69-78, 1995.
Chen et al., "Regulation of human cardiac myosin heavy chain genes: the effect of catecholamine," *Biochemical and Biophysical Research Communications*, 188(2):547-553, 1992.
Coffin et al., "Gene delivery to the heart in vivo and to cardiac myocytes and vascular smooth muscle cells in vitro using herpes virus vectors," *Gene Therapy*, 3:560-566, 1996.
Colucci and Branwald, In: *Heart Disease: A Textbook of Cardiovascular Medicine*, (Braunwald ed., 5th ed.), Chapter 13, 406, 1997.
Davidson et al., "Cardiac gene delivery with cardiopulmonary bypass," *Circulation*, 104:131-133, 2001.
del Monte et al., "Improvement in survival and cardiac metabolism after gene transfer of sarcoplasmic reticulum ca2+-ATPase in a rat model of heart failure," *Circulation*, 104:1424-1429, 2001.
Feldman et al., "Selective gene expression in failing human heart," *Circulation*, 83(6):1866-1872, 1991.
Flink et al., "Atrial and ventricular cardiac myosins contain different heavy chain species," *FEBS Letters*, 94(1):125-130, 1978.
Flink et al., "Interaction of thyroid hormone receptors with strong and weak sis-acting elements in the human α-myosin heavy chain gene promoter," *Journal of Biological Chemistry*, 265(19):11233-11237, 1990.
Fromes et al., "Gene delivery to the myocardium by intrapericardial injection," *Gene Therapy*, 12;683-688, 1999.
Gustafson et al., "Thyroid hormone regulated expression of a transfected α-myosin heavy-chain fusion gene in fetal heart cells," *Proc. Natl. Acad. Sci., USA*, 84:3122-3126, 1987.
Hajjar et al., "Modulation of ventricular function through gene transfer in vivo," *Proc. Natl. Acad. Sci., USA*, 95:5251-5256, 1998.
Hanatani et al., "Inhibition by angiotensin II type 1 receptor antagonist of cardiac phenotypic modulation after myocardial infarction," *J. Mol. Cell Cardiol.*, 27:1905-1914, 1995.
Hixson et al., "α-myosin heavy chain cDNA structure and gene expression in adult, fetal, and premature baboon myocardium," *J. Mol. Cell Cardiol.*, 21:1073-1086, 1989.
Izumo et al., "Myosin heavy chain messenger RNA and protein isoform transitions during cardiac hypertrophy," *J. Clin. Invest.*, 79:970-977, 1987.
Jones et al., "Ablation of the murine α myosin heavy chain gene leads to dosage effects and functional deficits in the heart," *J. Clin. Invest.*, 98:1905-1917, 1996.
Kashani-Sabet et al., "Detection of drug resistance in human tumors by in vitro enzymatic amplification," *Cancer Research*, 48:5775-5778, 1988.

(Continued)

*Primary Examiner*—Shin-Lin Chen
(74) *Attorney, Agent, or Firm*—Fulbright & Jaworski LLP

(57) ABSTRACT

The invention provides a method of treating myocardial failure in a human. The method comprises administering an effective amount of transgene encoding α-MHC that directly causes an increase in the quantity of α-MHC in the myocardial tissue of the heart.

1 Claim, 1 Drawing Sheet

OTHER PUBLICATIONS

Katz, "Cardiomyopathy of overload," *New England J. of Medicine*, 322(2):100-110, 1990.

Kurabayashi et al., "Molecular cloning and characterization of human cardiac α- and β-form myosin heavy chain complementary DNA clones," *J. Clin. Inves.*, 82:524-531, 1988.

Kurabayashi et al., "The myosin gene switching in human cardiac hypertrophy," *Japanese Circulation Journal*, 54:1192-1205, 1990.

Kypson et al., "Ex vivo adenovirus-mediated gene transfer to the adult rat heart," *J. Thorac. Surg.*, 115:623-630, 1998.

Ladenson et al., "Reversible alterations in myocardial gene expression in a young man with dilated cardiomyopathy and hypothyroidism," *Proc. Natl. Acad. Sci., USA*, 89:5251-5255, 1992.

Lazarous et al., "Adenoviral-mediated gene transfer induces sustained pericardial VEGF expression in dogs: effect on myocardial angiogenesis," *Cardiovasc. Res.*, 44:294-302, 1999.

Lee et al., "Cardiac gene transfer by intracoronary infusion of adenovirus vector-mediated reporter gene in the transplanted mouse heart," *J. Thorac. Cardiovasc. Surg.*, 111:246-252, 1996.

Lenhart et al., "Preservation of myocardial function after adenoviral gene transfer in isolated myocardium," *Am. J. Physiol. Heart Circ. Physiol.*, 279:H986, 2000.

Lévesque et al., "Determination of changes in specific gene expression by reverse transcription PCR using interspecies mRNAs as internal standards," *Biotechniques*, 17(4):738-741, 1994.

Li et al., "Efficient and long-term intracardiac gene transfer in δ-sarcoglycan-deficiency hamster by adeno-associated virus-2 vectors," *Gene Ther.*, 21:1807-1813, 2003.

Lin et al., "Expression of recombinant genes in myocardium in vivo after direct injection of DNA," *Circulation*, 82:2217-2221, 1990.

Lowes et al., "Assessment of gene expression in endomyocardial biopsy specimens from failing and nonfailing human hearts," *J. Investigative Med.*, Abstracts, 316A, 1995.

Lowes et al., "Downregulation of α-and upregulation of β-myosin heavy chain in intact, failing human ventricles," Abstract, American College Cardiol. 46th Annual Scientific Session, Feb. 1997.

Lowes et al., "Changes in gene expression in the intact human heart," *J. Clin. Invest.*, 100(9):2315-2324, 1997.

Minobe et al., "In vivo measurement of myocardial gene expression in the human heart," *JACC*, 277A, 1995.

Mittman et al., "Analysis of gene expression patterns in small amounts of human ventricular myocardium by a multiplex Rnase protection assay," *J. Mol. Med.*, 76:133-140, 1998.

Morkin et al., "Regulation of human cardiac myosin heavy chain gene expression by thyroid hormone," *Cellular and Molecular Mechanisms in Hypertension*, 143-147, 1991.

Morkin et al., "Regulation of myosin heavy chain genes in the heart," *Circulation*, 87(5):1451-1460, 1993.

Morkin et al., "Biochemical and physiologic effects of thyroid hormone on cardiac performance," *Progress in Cardiovascular Disease*, 25(5):435-464, 1983.

Morkin et al., "Replacement of myosin during development of cardiac hypertrophy," *Supplement III to Circulation Research*, 34 & 35:111-50-111-57, 1974.

Nagai et al., "Myosin isozyme synthesis and mRNA levels in pressure-overload rabbit hearts," *Circulation Research*, 60:692-699, 1987.

Nakao et al., "Alpha myosin heavy chain gene expression in nonfailing and end-stage failing human left ventricles," *J. Clin. Invest.*, 100(9):2362-2370, , 1997.

O'Donnell et al., "Tight control of exogenous SERCA expression is required to obtain acceleration of calcium transients with minimal cytotoxic effects in cardiac myocytes," *Circ. Res.*, 88:415-421, 2001.

Pachucki et al., "Type 2 iodothyronin deiodinase transgene expression in the mouse heart causes cardiac-specific thyrotoxicosis," *Endocrinology*, 142:13, 2001.

Pennock et al., "Cardiac effects of 3,5-diiodothyropropionic acid, a thyroid hormone analog with inotropic selectivity," *Journal of Pharmacology and Experimental Therapeutics*, 263(1):163-169, 1992.

Rench et al., "Adolescents and health heart living," *Fla Nurse.*, 49(3):16, 2001.

Schroder et al., "Immune response after adenoviral gene transfer in syngenic heart transplants: effects of anti-CD4 monoclonal antibody therapy," *Transplantation*, 70:191-198, 2000.

Shinmura et al., "Catheter-Delivered in vivo gene transfer into rat myocardium using the fusigenic mediated method," *Japan Heart J.*, 41:633, 2000.

Silva et al., "Reduced cardiac hypertrophy and altered blood pressure control in transgenic rats with the human tissue kallikrein gene," *FASEB*, 14:1858, 2000.

Stratford-Perricaudet et al., "Widespread long-term gene transfer to mouse skeletal muscles and heart," *J. Clin. Invest.*, 90:626-630, 1992.

Tsika et al., "Thyroid hormone regulates expression of a transfected human α-myosin heavy-chain fusion gene in fetal rat heart cells," *Proc. Natl. Acad. Sci., USA*, 87:379-383, 1990.

Umeda et al., "Control of mysoin heavy chain expression in cardiac hypertrophy," *Am. J. Cardiol.*, 59:49A-55A, 1987.

Umeda et al., "Sequences of the rabbit beta myosin heavy chain promoter produce a condition of chronic heart failure in transgene mice," *Circulation*, Suppl., 84(8): 1408, Abatract 2378, 1996.

von Harsdorf et al., "Gene injection into canine myocardium as a useful model for studying gene expression in the heart of large mammals," *Circ. Res.*, 72:688-695, 1993.

Vrana et al., "Application of quantitative RT-PCR to the analysis of dopamine levels in rat striatum," *Molecular Brain Research*, 34:127-134, 1995.

Wang et al., "Quantitation of mRNA by the polymerase chain reaction," *Proc. Natl. Acad. Sci., USA*, 86:9717-9721, 1989.

Wickenden et al., "Targeted expression of a dominant-negative K(v)4.2 K(+) channel subunit in the mouse hea," *Circu. Res.*, 85:1067, 1999.

Yue et al., "Microdystrophin Gene Therapy of Cardiomyopathy Restores Dystrophin-Glycoprotein Complex and Improves Sarcolemma Integrity in the Mdx Mouse Heart," *Circulation*, 2003.

GenBank Accession No. D00943, Oct. 20, 1992.

GenBank Accession No. X52889, Sep. 14, 1993.

Khoury et al., "Effects of thyroid hormone on left ventricular performance and regulation of contractile and Ca2+-cycling proteins in the baboon," *Circulation Research*, 79(4):727-735, 1996.

Ladenson et al., "Reversible alterations in myocardial gene expression in a young man with dilated cardiomyopathy and hypothyroidism," *Proc. Natl. Acad. Sci., USA*, 89:5251-5255, 1992.

Lompre et al., "Expression of the cardiac ventricular α- and β-myosin heavy chain genes is developmentally and hormonally regulated," *J. Biol. Chem.*, 259(10):6437-6446, 1984.

Lowes et al., "Changes in gene expression in the intact human heart: downregulation of α-yosin heavy chain in hypertrophied failing ventricular myocardium," *J. Clin. Invest.*, 100(9):2315-2321, 1997.

Moruzzi et al., "Medium-term effectiveness of L-thyroxine treatment in idiopathic dilated cardiomyopathy," *Am. J. Med.*, 101:461-467, 1996.

Weiss and Leinwand, "The mammalian myosin heavy chain gene family," *Annu. Rev. Cell Dev. Biol.*, 12:417-439, 1996.

Japanese Office Action, issued in Japanese Patent Application No. 10-533182, dated Oct. 2, 2007.

Matsuoka et al., "Complete sequence of human cardiac alpha-myosin heavy chain and amino acid comparison to other myosins based on structural and functional differences," *Am. J. Med. Genet.*, 41:537-547, 1991.

* cited by examiner

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "primer"

(xi) SEQUENCE DESCRIPTION: SEQ ID NO: 1:

ATCAAGGAGC TCACCTACCA G                    21

(2) INFORMATION FOR SEQ ID NO: 2:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 2:

CTTTTACGTG CTACTCCTCA C                                                   21

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 3:

GACCTCGGAC ACATTGTCGA                                                     20

(2) INFORMATION FOR SEQ ID NO: 4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 4:

ATCAAGGAGC TCACCTACCA GGTGAGGAGT AGCACGTAAA AG                            42

(2) INFORMATION FOR SEQ ID NO: 5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 5:

CTTTTACGTG CTACTCCTCA CCTGGTAGGT GAGCGCCGGG AT                            42

(2) INFORMATION FOR SEQ ID NO: 6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 6:

ATCAAGGAGC TCACCTACCA GTCGACAATG TGTCCGAGGT C                             41
```

-continued (2) INFORMATION FOR SEQ ID NO: 7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 7:

```
GACCTCGGAC ACATTGTCGA CTGGTAGGTG AGCGCCGGGA T                    41
```

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 8:

```
AGCAGAAGCG CAACGCAGAG T                                          21
```

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 9:

```
TGCTGCACCT TGCGGAACTT G                                          21
```

DIAGNOSIS AND TREATMENT OF MYOCARDIAL FAILURE

This is a divisional of U.S. application Ser. No. 09/016,075, filed Jan. 30, 1998, now abandoned, which claims priority to U.S. Provisional Application Ser. No. 60/038,911, filed Feb. 26, 1997, and U.S. Provisional Application Ser. No. 60/036,987, filed Jan. 30, 1997.

This invention was made with government support under NIH grants 5R37 HL 50530-04, RO1 HL 48013, and GCRC-CAP 5 MO 1 RR00051. The government has certain rights in the invention.

FIELD OF THE INVENTION

The present invention relates to a method of diagnosing myocardial failure in humans by quantitating the expression of α-myosin heavy chain (α-MHC), β-myosin heavy chain (β-MHC), or both in a sample of myocardial tissue from a ventricle of the heart. The invention further relates to a method of treating myocardial failure in aging humans or humans suffering from heart failure by increasing the expression of α-MHC in myocardial tissue.

BACKGROUND OF THE INVENTION

Heart failure is a pathophysiological state in which the heart fails to pump blood at a rate commensurate with the requirements of the metabolizing tissues of the body. It is caused in most cases (about 95% of cases) by myocardial failure.

The contractile proteins of the heart lie within the muscle cells (myocytes), which constitute about 75% of the total volume of the myocardium. The two major contractile proteins are the thin actin filament and the thick myosin filament. Each myosin filament contains two heavy chains and four light chains. The bodies of the heavy chains are intertwined, and each heavy chain ends in a head. Each lobe of the bilobed myosin head has an ATP-binding pocket, which has in close proximity the myosin ATPase activity that breaks down ATP to its products.

The velocity of cardiac muscle contraction is controlled by the degree of ATPase activity in the head regions of the myosin molecules. The major determinant of myosin ATPase activity and, therefore, of the speed of muscle contraction, is the relative amounts of the two myosin heavy chain isomers, alpha and beta (α-MHC and β-MHC). The α-MHC isoform has approximately four times more enzymatic activity than the β-MHC isoform and, consequently, the velocity of cardiac muscle shortening is related to the relative percentages of each isoform. For example, adult rodent ventricular myocardium has approximately 80-90% α-MHC and only 10-20% β-MHC, which explains why its myosin ATPase activity is 3-4 times greater than bovine ventricular myocardium, which contains 80-90% β-MHC.

When ventricular myocardial hypertrophy or heart failure is created in rodent models, a change occurs in the expression of MHC isoforms, with α-MHC decreasing and β-MHC becoming the dominant isoform. These "isoform switches" then reduce the contractility of the hypertrophied rodent ventricle, ultimately leading to myocardial failure. This pattern of altered gene expression has been referred to as reversion to a "fetal" pattern because, during fetal and early neonatal development, β-MHC also dominates in rodent ventricular myocardium.

Although human atrial myocardium may undergo similar isoform switches with hypertrophy or failure, human ventricular myocardium, the basis for the majority of cases of heart failure (greater than 90% of cases), has not been thought to exhibit this pattern. This is because several studies which examined this issue in autopsy cases did not find biologically significant expression of the α-MHC isoform in putatively normal hearts. Since there was thought to be no significant expression of α-MHC in normal hearts, a downregulation in α-MHC was not thought to be a possible basis for myocardial failure in humans. There has been one report that the amount of α-MHC, although extremely small to begin with, is reduced in failing human myocardium. Bouvagnet et al., *Basic Res. Cardiol.*, 84, 91-102 (1989). There have also been conflicting reports about the presence and amounts of α-MHC and β-MHC messenger RNA (mRNA) in normal and failing human myocardium. Cf. Arai et al., *Circ. Res.*, 72, 463 (1993) with Lowes et al., *J. Invest. Med.*, 43, 316A (1995). However, as of 1997, those skilled in the art still considered it unlikely that a shift in myosin isoforms occurred in human myocardial failure. See Colucci and Braunwald, in *Heart Disease: A Textbook of Cardiovascular Medicine* (Braunwald ed., 5th ed., 1997), Chapter 13 at page 406. Indeed, MHC gene expression is considered to be a classical example of species variation in the expression of genes, and data on MHC gene expression in human disease states cannot be extrapolated from animal studies.

It has been shown that myocardial function declines with age in animals. Cellular and molecular mechanisms that account for age-associated changes in myocardial performance have been studied largely in rodents. Among other changes, marked shifts in MHC occur in rodents, i.e., the β isoform becomes predominant in senescent rats (85% β versus 15% α). Steady-state mRNA levels for α-MHC and β-MHC parallel the age-associated change in the MHC proteins. The myosin ATPase activity declines with the decline in α-MHC content, and the altered cellular profile results in a contraction that exhibits a reduced velocity and a prolonged time course. No similar studies are known to have been made in humans and, as noted above, data on MHC gene expression from animal studies cannot be extrapolated to humans.

For a detailed discussion of heart failure, MHC gene expression, and age-associated changes in cardiac performance, see *Heart Disease: A Textbook of Cardiovascular Medicine* (Braunwald ed., 5th ed., 1997).

SUMMARY OF THE INVENTION

The invention provides a method of diagnosing myocardial failure in a human. The method comprises obtaining a sample of myocardial tissue from a ventricle of the heart of the human. The expression of α-myosin heavy chain (α-MHC), β-myosin heavy chain (β-MHC), or both in the sample is quantitated. Then, it is determined by statistical analysis if the expression of α-MHC, β-MHC, or both in the sample is significantly different than their expression in normal human ventricular myocardial tissue.

The invention also provides a kit for diagnosing myocardial failure in a human. The kit comprises a container holding at least one nucleic acid molecule that hybridizes to DNA or RNA coding for α-MHC, β-MHC or both.

The invention further provides a method of treating myocardial failure in a human. The method comprises administering an effective amount of an agent that directly causes an increase in the quantity of α-MHC in the myocardial tissue of the heart.

Finally, the invention provides a method of quantitating the expression of a first protein relative to the expression of a second protein or to the total expression of the first and second proteins. The method comprises obtaining a sample of cells or tissue expressing the first protein and the second protein, extracting RNA from the cells or tissue, preparing cDNA from the RNA, amplifying the cDNA coding for the first and second proteins by polymerase chain reaction using primers that hybridize to cDNA coding for the first protein, the second protein or both, and quantitating the amplified PCR products.

DETAILED DESCRIPTION OF THE PRESENTLY PREFERRED EMBODIMENTS OF THE INVENTION

Figure 1A:
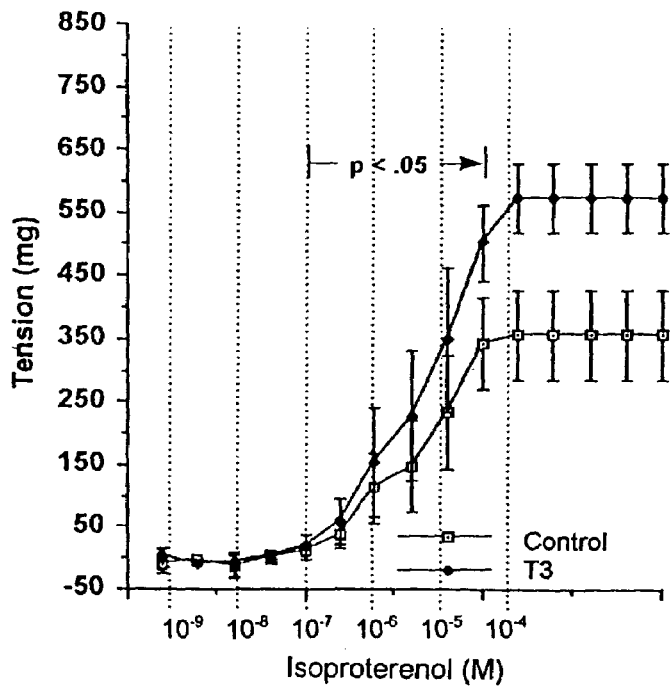
FIGS. 1A-B: Graphs showing the effect of a four-hour (FIG. 1A) or a twelve-hour (FIG. 1B) incubation with 1 nM triodothyronine (T3) on peak systolic tension response to isoproterenol in isolated right ventricular trabeculae removed from end-stage failing human hearts.
Figure 1B:
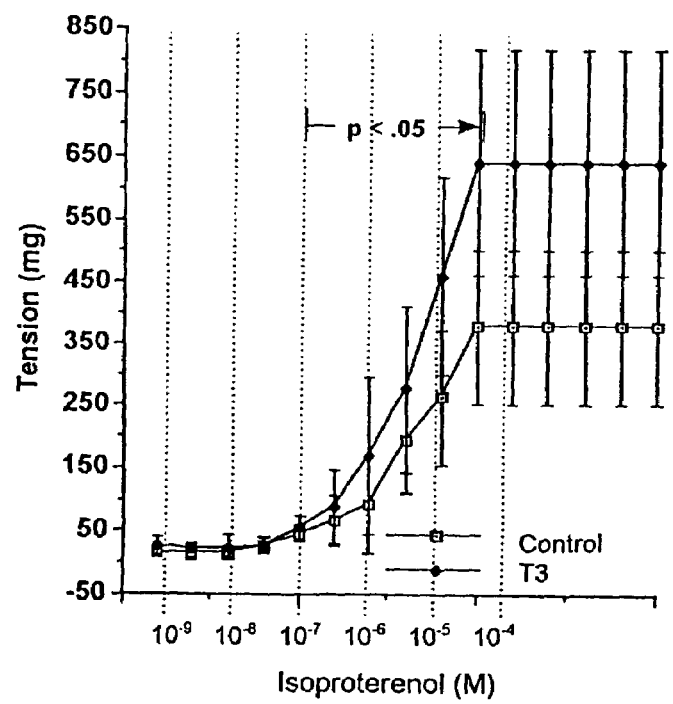

The invention provides a method of diagnosing myocardial failure in a human. "Myocardial failure" means a defect in myocardial contraction or an abnormality of myocardial function. As noted above, myocardial failure is the cause of most cases (greater than 90% of cases) of heart failure, and it occurs in aging hearts.

The diagnostic method of the invention comprises quantitating the expression of α-MHC, β-MHC, or both in a sample of myocardial tissue taken from ventricular myocardium. It has been found that the expression of α-MHC and β-MHC in the left ventricle is similar to that in the right ventricle when the function of the two ventricles is similar (see Example 3 below). Since myocardial failure occurs in both ventricles in aging and in most cases of heart failure, it is expected that, in most cases, either ventricle can be used as a sampling site. Although, the left ventricle is of primary importance because it is responsible for pumping blood to all of the tissues of the body, except the lungs, the right ventricle will generally be used as the sampling site because of ease of sampling. In cases where only the right ventricle is suspected of failing (e.g., in primary pulmonary hypertension), then the right ventricle must be sampled. Similarly, in cases where only the left ventricle is suspected of failing (e.g., subsequent to myocardial infarction in the left ventricle), then the left ventricle must be sampled.

The sample of ventricle tissue to be tested is preferably procured from a living patient by endomyocardial biopsy, a technique well known in the art. See Wynne and Braunwald, in *Heart Disease: A Textbook of Cardiovascular Medicine* (Braunwald ed., 5th ed., 1997), Chapter 41 at pages 1404-1406. The tissue sample may also be obtained from hearts removed at autopsy or prior to transplantation of replacement hearts.

The diagnostic method of the invention may be used to make a diagnosis of a patient's condition. The method may also be used to assess the effectiveness of the drugs or other measures used to treat a patient diagnosed as suffering from myocardial failure.

The expression of α-MHC, β-MHC, or both in the test sample must be compared with their expression in normal ventricular myocardial tissue from age-matched controls. The normal tissue should be from the same ventricle as the test sample. The comparison is made using standard methods of statistical analysis well known in the art.

The normal tissue samples can be obtained from hearts removed from individuals dying of non-cardiac causes, primarily accidental deaths and homicides. For instance, samples from explanted hearts intended, but not used, for transplantation can be used. Alternatively, myocardial biopsy samples from living donors can be used. For instance, myocardial biopsy samples from patients suspected of having heart disease, but subsequently determined to be normal, can be used (see Example 1). Also, the normal values set forth in the examples below may be used for comparison purposes.

"Normal" and "nonfailing" are used herein interchangeably. Both are intended to mean that the hearts show no signs of myocardial failure and appear to function normally.

A diagnosis of myocardial failure can be made if the statistical analysis shows: (1) that the expression of α-MHC in the test sample is significantly lower than it is in the age-matched normal tissue; (2) that the expression of β-MHC in the test sample is significantly higher than it is in the age-matched normal tissue; (3) both of these; or (4) the ratio of α-MHC expression to β-MHC expression or total MHC expression (α-MHC/β-MHC or α-MHC/α-MHC+β-MHC) is significantly less than in age-matched normal tissue.

The expression of α-MHC, β-MHC, or both is preferably measured by quantitating mRNA levels, preferably by polymerase chain reaction (PCR). MHC mRNA and protein levels are closely correlated (see Nadal-Grinard et al., *J. Clin. Invest.*, 84, 1693-1700 (1989)), and quantitative PCR is an extremely sensitive technique.

To perform the PCR assay, mRNA is obtained from a sample of ventricular myocardial tissue and used to synthesize cDNA. Methods of extracting total cellular RNA from tissue and of preparing cDNA are well known.

Next, the cDNA coding for α-MHC, β-MHC, or both is amplified by PCR. PCR methods, equipment, and reagents are well known and are available commercially.

The primers used in the PCR amplification should have sequences selected so that they hybridize to one of the strands of the cDNA coding for α-MHC, β-MHC, or both. Methods of making nucleic acid molecules of a desired sequence are well known in the art. Of course, at least two primers must be used (one hybridizing to each of the strands of the cDNA), but more than one pair of primers can be used if it is desired to amplify more than one portion of the cDNA. The primers should be at least 18-20 bp in length with a G+C content greater than 40%. The specificity of the primers should be confirmed by Southern blotting.

Finally, the amplified PCR product is quantitated. This can be accomplished in a number of ways as is known in the art. For instance, the reaction mixture can be electrophoresed on agarose gels, and the amount of amplified PCR product of the expected size(s) can be determined. A labeled probe which hybridizes to an amplified PCR product can be used to allow for quantitation of the amplified PCR product. As another alternative, the primers can be labeled, or the nucleotides used during the PCR can be labeled, and the labels incorporated into the amplified PCR product can be quantitated.

As noted above, the probes or primers may be labeled to allow for quantitation of the cDNA coding for α-MHC, β-MHC, or both. Suitable labels and methods of attaching or incorporating them into nucleic acid molecules are well known. Suitable labels include radioactive labels (e.g., $^{32}P$), chemiluminescent labels, fluorescent labels (e.g., fluorescein, rhodamine), particulate labels (e.g., gold colloids), colorimetric labels (e.g., dyes), enzymes, and biotin.

As also noted above, labeled nucleotides can be used during PCR to generate an amplified PCR product which is labeled. The nucleotides are preferably labeled with radioactive labels (e.g., $^{32}P$) by methods well known in the art.

The quantities of the amplified PCR products are then related to the level of expression of α-MHC, β-MHC, or both in the sample. Then, it is determined by statistical analysis if the expression of α-MHC, β-MHC, or both in the sample is significantly different than their expression in normal human ventricular myocardial tissue.

For instance, two particularly preferred PCR assays are those described in Examples 1 and 3 below. In the assay described in Example 1, an internal standard cRNA transcribed from a synthetic gene is used to assure accurate quantitation of mRNA, and the levels of α-MHC and β-MHC mRNAs in sample and normal tissue are compared statistically. The assay described in Example 3 only provides a ratio of α-MHC expression to total MHC expression (α-MHC/α-MHC+β-MHC), not absolute quantities of mRNA, and the ratios for sample and normal tissue are compared statistically. The assay described in Example 3 it is a relatively simple PCR assay to perform, and it may also be used to quantitate other pairs of proteins besides α-MHC and β-MHC (see discussion below).

The mRNA coding for α-MHC, β-MHC, or both, can also be quantitated by contacting the mRNA, or cDNA prepared from it, with a nucleic acid probe having a sequence selected so that the molecule hybridizes to mRNA or cDNA coding for α-MHC, β-MHC or both. To quantitate the mRNA, the probe is labeled. The probe should be as large as possible while retaining specificity. The probes may be made and labeled as described above for the primers. Stringent hybridization conditions should be employed. In particular, it has been found that the 3' untranslated regions of the mRNAs coding for α-MHC and β-MHC have different lengths and substantially different sequences (see Kurabayashi et al., *J. Clin. Invest.*, 82, 524-531 (1988)), and probes directed to these regions are preferred. The probes may also be used in an RNAse protection assay, such as described in Bristow et al., *J. Clin. Invest.*, 92, 2737-2745 (1993).

The invention also provides a kit containing reagents useful for diagnosing myocardial failure. The kit comprises at least one container holding at least one nucleic acid molecule that hybridizes to DNA or RNA coding for α-MHC, β-MHC or both. The nucleic acid molecule may be a PCR primer or a probe. The probes and primers may be labeled. The kit may comprise one or more additional containers holding additional probes or primers or an internal standard cRNA. The kit may contain other reagents and equipment useful in performing the assay, including PCR reagents (e.g., polymerase, labeled or unlabeled nucleotides), reagents for extraction of mRNA, reagents for synthesizing cDNA from mRNA, buffers, salt solutions, containers, gels and membranes, etc.

Techniques other than those described above have been used to quantitate α-MHC and β-MHC, and it may be possible to use these techniques in the method of the invention. However, as shown by the discussion in the Background section, these techniques may not have accurately determined the expression of α-MHC and β-MHC in human myocardial tissue. Thus, the accuracy of these techniques must be determined, and the sensitivity and/or specificity of the techniques may need to be increased, before using them.

The invention also provides a method of treating myocardial failure in a human. The method comprises administering an effective amount of an agent that directly causes an increase in the quantity of α-MHC in the myocardial tissue of the heart.

"Directly causing" is used herein to mean that the agent acts directly to increase the transcription of the α-MHC gene or to increase the translation of α-MHC mRNA by binding to the α-MHC gene, to an mRNA transcript of the gene, to a protein which binds to the gene or mRNA transcript, or to a compound which binds to the gene, mRNA transcript or a protein which binds to the gene or mRNA transcript. For instance, the agent may initiate or enhance transcription of the α-MHC gene by binding to an enhancer element of the α-MHC gene or to a transcription factor bound to an enhancer element of the gene. The agent could also stabilize the mRNA transcript, or bind to a compound that represses transcription, thereby blocking repression of transcription. Human α-MHC genomic and cDNA clones have been isolated, and some information is known about the regulation of α-MHC gene expression. See Kurabayashi et al., *J. Clin. Invest.*, 82, 524-531 (1988); Tsika et al., *Proc. Natl. Acad. Sci. USA*, 87, 379-383 (1990); Flink et al., *J. Biol. Chem.*, 265, 11233-1137 (1990); Chen et al., *Biochem. Biophys. Res. Commun.*, 188, 547-553 (1992); Morkin, *Circulation*, 87, 1451-1460 (1993). "Directly causing" is also used herein to mean that the agent acts directly to decrease the breakdown of the α-MHC protein by, e.g., binding to the α-MHC protein or to a compound that degrades or inactivates the α-MHC protein. Of course, a combination of agents, or a single agent, that performs two or more of the above functions (increases transcription, increases translation, decreases breakdown of protein) may be used.

As shown below, treatment of heart failure by blockade of β-adrenergic receptors results in increased expression of α-MHC and improved myocardial function. However, such treatments which increase the quantity of α-MHC indirectly as a result of the improved myocardial function caused by the treatment are not included within the invention.

Agents that directly cause an increase in the quantity of α-MHC include thyroid hormones and analogs thereof. For instance, $T_3$ (3,5,3'-triiodo-L-thyronine) or $T_4$ (3,3',5,5'-tetraiodo-L-thyronine) may be used. One suitable thyroid hormone analog is 3,5-diiodothyroproprionic acid, an analog known to increase the production of α-MHC in hypothyroid rats. Pennock et al., *J. Pharmacol. Exp. Therapeutics*, 263, 163-169 (1992). Pharmaceutical preparations of thyroid hormone are available commercially, and these commercially-available preparations may be used in the practice of the invention. See *Physicians Desk Reference*. Preferred is the synthetic thyroid hormone Synthroid.

Other suitable agents that directly cause an increase in the quantity of α-MHC can be identified using methods well known in the art. See, e.g., U.S. Pat. No. 5,580,722 and Morkin, *Circulation*, 87, 1451-1460 (1993), the complete disclosures of which are incorporated herein by reference.

To treat a patient suffering from myocardial failure, an effective amount of an agent that directly causes an increase in the quantity of α-MHC in the myocardial tissue of the heart is administered to the patient. Effective dosage forms, modes of administration and dosage amounts, may be determined empirically, and making such determinations is within the skill of the art. It is understood by those skilled in the art that the dosage amount will vary with the activity of the particular agent employed, the severity of the myocardial failure, the route of administration, the rate of excretion, the duration of the treatment, the identity of any other drugs being administered to the patient, the age and size of the patient, and like factors well known in the medical art. In general, a suitable daily dose of an agent of the present invention will be that amount of the agent which is the lowest dose effective to produce a therapeutic effect. A suggested daily dosage of thyroid hormone for treatment of myocardial failure is about 50-200 μg/day of synthetic thyroid hormone (e.g., Synthroid). However, the total daily dosage of the agent will be determined by an attending physician within the scope of sound medical judgment. If desired, the effective daily dose may be administered as two, three, four, five, six or more sub-doses, administered separately at appropriate intervals throughout the day.

The agents of the present invention may be administered to a patient for therapy by any suitable route of administration, including orally, parenterally, and topically. The preferred route of administration is orally.

While it is possible for an agent of the present invention to be administered alone, it is preferable to administer the compound as a pharmaceutical formulation (composition). The pharmaceutical compositions of the invention comprise one or more of the agents of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the patient. Suitable carriers are well known in the art.

Pharmaceutical formulations of the present invention include those suitable for oral, topical and/or parenteral administration. Regardless of the route of administration selected, the agents of the present invention, are formulated into pharmaceutically-acceptable dosage forms by conventional methods known to those of skill in the art.

The amount of active ingredient which will be combined with a carrier material to produce a single dosage form will vary depending upon the host being treated, the particular mode of administration and all of the other factors described above. The amount of active ingredient which will be combined with a carrier material to produce a single dosage form will generally be that amount of the agent which is the lowest dose effective to produce a therapeutic effect.

Methods of preparing pharmaceutical formulations or compositions include the step of bringing into association an agent of the present invention with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product. Suitable and necessary accessory ingredients are well known in the art.

Another embodiment of the present invention is the treatment of myocardial failure by gene therapy to increase α-MHC expression. The gene therapy method of the invention comprises delivering a transgene coding for α-MHC to a human so that the α-MHC is expressed in at least the myocardial tissue of the heart of the recipient. Thus, "agents that directly cause an increase in the quantity of α-MHC in the myocardial tissue of the heart" include transgenes coding for α-MHC.

The α-MHC transgene is constructed and cloned by standard methods known in the art. Such standard methods are disclosed, for example, in Sambrook et al., 1989, *Molecular Cloning: A Laboratory Manual*, Cold Spring Harbor Labs Press. The reference Sambrook et al., ibid., is incorporated herein by reference in its entirety.

As noted above, genomic and cDNA clones coding for human α-MHC are known. Other clones can be isolated using standard methods known in the art. Alternatively, DNA coding for human α-MHC can be synthesized by chemical synthetic methods known in the art using the known sequence. The transgene may contain a single copy or multiple copies of the α-MHC coding sequence (increasing the copy number of the coding sequence will increase expression of α-MHC).

In addition to the DNA coding for α-MHC, the transgene is constructed to include a promoter selected to drive expression of the α-MHC exclusively in the heart and in at least the myocardial tissue. Preferably, the promoter is an α-MHC promoter.

In addition to the promoter, the transgene will contain other expression control sequences necessary or desirable for proper expression and processing of the α-MHC. These expression control sequences and the promoter will be operatively linked to the α-MHC-encoding DNA. The phrase "operatively linked" refers to linking of nucleic acid sequences in the transgene in a manner such that the α-MHC can be expressed in cardiac cells when the transgene is integrated into a host genome. The additional expression control sequences are well known in the art and include sequences which control the initiation, elongation, and termination of transcription (such as enhancer sequences and polyadenylation sequences).

Methods and materials for gene therapy are well known in the art. See Culver, *Gene Therapy: A Primer for Physicians* (Revised 2nd ed., 1996), U.S. Pat. Nos. 5,521,291, 5,460,831 and 5,559,099, PCT application WO 96/14876, all of which are incorporated herein by reference in their entirety. See also, Kirshenbaum, et al., *J. Clin. Invest.*, 92, 381-387 (1993) and Drazner et al., *J. Clin. Invest.*, 99, 288-296 (1997). In particular, suitable methods and vehicles for delivery of transgenes are known and may be used to deliver the α-MHC transgene. For instance, naked DNA can be injected directly into the myocardium. Also, targeted vehicles may be used for delivery of the transgene to myocytes. A targeted vehicle is one which includes a component that allows the vehicle to bind to, and deliver the transgene to, a specific cell or tissue. Such targeted vehicles are known in the art. The transgene may be included in a viral vector for delivery to myocytes. Such viral vectors are known in the art. Preferably, the transgene is incorporated into an adenoviral vector for delivery. See Kitsis, et al., *Proc. Natl. Acad. Sci. USA*, 88, 4138-4142 (1991); Kass-Eisler et al., *Proc. Natl. Acad. Sci. USA*, 90, 11498-11502 (1993); Akhter, et al., *Proc. Natl. Acad. Sci. USA*, 94, 12100-12105 (1997). The transgene is preferably infused directly into the heart by injecting it into the coronary artery, thereby ensuring the greatest amount of transgene absorption into myocytes. The transgene preferably integrates into the host cell's genome to provide for stable transformation.

Finally, the invention provides a method of quantitating the expression of a first protein relative to the expression of a second protein or to the total expression of the first and second proteins. The method comprises obtaining a sample of cells or tissue expressing the first protein and the second protein, extracting RNA from the cells or tissue, preparing cDNA from the RNA, amplifying the cDNA coding for the first and second proteins by PCR using primers that hybridize to cDNA coding for the first protein, the second protein or both, and quantitating the amplified PCR products. All of these techniques are described above.

The quantities of the amplified PCR products are then related to the levels of protein expression in the sample, and the expression of a first protein relative to the expression of a second protein or to the total expression of the first and second proteins is calculated. Then, it is determined by standard statistical analysis if the calculated relative expression of the first protein in the sample cells or tissue is significantly different than it is in normal cells or tissue.

Any pair of proteins can be quantitated in this manner, but the pair preferably have sequences similar enough so that the cDNAs coding for them can be amplified by the same pair of primers (so that any errors due to differences in primer efficiencies are readily avoided), but different enough so that the PCR products can be differentiated in some manner (e.g., size, different enzyme cleavage sites). Examples of such proteins include α-MHC and β-MHC (see Example 3), mutated and unmutated versions of the same protein (e.g., gene therapy), the same protein from different species (e.g., transgenic animals), proteins produced as a result of alternate splicing. For less similar proteins, differences in PCR conditions and primer efficiencies must be accounted for. For instance, one of the proteins of the protein pair could be one whose expression is not expected to change under the conditions being studied. For example, sacroplasmic reticulum $Ca^{2+}$ ATPase (SRCA) expression does not change significantly in failing hearts as compared to normal hearts (see Examples 1-3 and 5), and changes in the ratio of α-MHC expression to SRCA expression should accurately reflect changes in α-MHC expression.

EXAMPLES

Example 1

Measurement of Expression of MHC Isoforms in Endomyocardial Tissue by PCR

The amount of mRNA coding for α-MHC, β-MHC, $β_1$-adrenergic receptor ($β_1$AR), $β_2$-adrenergic receptor ($β_2$AR), sacroplasmic reticulum $Ca^{2+}$ ATPase (SRCA), and atrial natriuretic factor or peptide (ANP) in total mRNA extracted from endomyocardial biopsy specimens was measured by quantitative PCR. The endomyocardial specimens were taken from the hearts of 29 subjects with biventricular failure from idiopathic dilated cardiomyopathy (IDC), 7 subjects with right ventricular failure from primary pulmonary hypertension (PPH), and 8 nonfailing (NF) controls.

The IDC and PPH donors were all ambulatory subjects who were not end-stage from the standpoint of clinical condition or intravenous inotropic support. Five of the PPH patients were New York Heart Association (NYHA) class III, one was class II, and one was class IV. Twenty-one of the IDC patients were NYHA class III, five were class II, and three were class IV.

The NF control samples were obtained from: five cancer patients about to begin chemotherapy with IL-4 or liposomal adriamycin; two subjects with normal systolic function and atypical chest pain or unexplained dyspnea on exertion who were biopsied to rule out myocarditis or cardiomyopathy; and a subject with normal right ventricle function and minimal left ventricle dysfunction who was biopsied to rule out an infiltrative mycoardial process 72 hours after being resuscitated from a cardiac arrest that was ultimately attributed to coronary artery spasm. Six of the NF controls were NYHA class I, one was NYHA class II, and the subject who had arrested returned to class I several weeks after being evaluated.

Hemodynamics for these tissue donors are given in Table 1 below. RVEF and LVEF are right ventricle ejection fraction and left ventricle ejection fraction, respectively, RA is right atrial mean pressure, PAP is pulmonary artery mean pressure, and PW is pulmonary wedge mean pressure.

Total RNA was extracted from 2-4 endomyocardial biopsies (a total of 4-8 mg) taken from distal right ventricle (RV) septum. The biopsies were performed with a Mansfield 2.2 mm jaw size (Boston Scientific Corp., Watertown, Mass.) bioptome under echocardiographic guidance to ensure proper positioning of the biopsy forceps. Total RNA was extracted by the guanididium thiocyanate phenol-chloroform method using RNA STAT-60, as previously described. Feldman et al., *Circulation*, 83, 1866-1872 (1991); Bristow et al., *J. Clin. Invest.*, 92, 2737-2745 (1993). A double extraction was used to eliminate small amounts of DNA contamination.

The mRNA was quantitated by PCR, as previously described in Feldman et al., *Circulation*, 83, 1866-1872 (1991) and Bristow et al., *J. Clin. Invest.*, 92, 2737-2745 (1993), the complete disclosures of which are incorporated herein by reference, with some modifications described below.

Briefly, this PCR technique (referred to herein as "RT-QPCR") is based on the simultaneous reverse transcription of an internal standard cRNA and an mRNA of interest, followed by simultaneous PCR amplification with the same primers of the cDNAs produced from the internal standard cRNA and mRNA of interest. The internal standard cRNA is designed to produce a cDNA of smaller size than the PCR product generated from the transcript of interest.

The internal standard cRNA is prepared by constructing a synthetic gene which contains a coding region comprising a DNA sequence complementary to the primers used to specifically amplify a region of the cDNA prepared from the mRNA that is to be measured. The synthetic gene is driven by the T7 RNA polymerase promoter, and in vitro transcription of the synthetic gene produces the internal standard cRNA. The synthetic gene also contains a polyadenine tract at its 3' end to facilitate reverse transcription. The internal standard cRNA is used as a template for reverse transcriptase in the same reaction that generates cDNA from the mRNA of interest, and a cDNA corresponding to the internal standard cRNA is produced along with the cDNA corresponding to the mRNA of interest.

One internal standard cRNA can be used to measure multiple (4-20) mRNAs by constructing a synthetic gene having a coding region comprising DNA sequences complementary to primers used to specifically amplify a region of each of the multiple cDNAs prepared from the mRNAs in the sample that are to be measured. Such a synthetic gene was used in the assays described in the present example. It contained sequences complementary to the mRNAs coding for α-MHC, β-MHC, $β_1$AR, $β_2$AR, SRCA and ANP. In particular, the gene's coding region contained sequences corresponding to that of the primers used to amplify the α-MHC, β-MHC, $β_1$AR, $β_2$AR, SRCA and ANP cDNAs. Thus, the cDNA generated from the internal standard cRNA could be amplified by the same primers used to amplify the cDNAs generated from the mRNAs of interest. However, the PCR products produced from the internal standard cDNA were smaller than the PCR products produced from the cDNAs generated from the mRNAs of interest.

When possible, the sequences of the primers were selected to cross splice junctions, so that genomic DNA would not be amplified. For intronless genes, such as those of the adrenergic receptors, the extreme sensitivity (into the zeptomole range) of the assay can lead to genomic DNA amplification. An RT(−) control (no reverse transcription) was included to detect this possibility.

Further, in the assay for $β_1$AR mRNA, the reverse transcription (RT) and PCR conditions were modified to increase the RT and amplification efficiencies, to eliminate significant genomic DNA contamination, and to obtain robust cDNA amplification in 30 PCR cycles or less. These modifications included double extraction of RNA with RNA STAT 60™ (Tel-Test, Friendswood, Tex.) and multiple changes in the RT assay conditions, including adding 2% DMSO, using oligo $d(T_{15})$ primers to gain specificity for mRNA, increasing the concentration of Moloney murine leukemia virus (MMLV) reverse transcriptase by 50%, and carrying out the RT reaction in a thermocycler. The thermocycler protocol included an initial 15 minutes at 37° C., ramping the temperature up to 45° C. over 15 minutes and holding it there for an additional 15 minutes, and finally inactivating the transcriptase at 95° C. for 10 minutes. With these modifications, a 202 bp region of the $β_1$AR cDNA reverse transcribed from mRNA in total RNA as the starting material was amplified in 30 cycles or less of PCR without genomic amplification. These modifications allowed for measurement of $β_1$AR mRNA abundance in total RNA extracted from small (1-3 mg) samples of human ventricular myocardium.

As determined using in vitro transcribed mRNA relative to the internal standard, the efficiency of reverse transcription was 7.5 times greater for $β_2$AR mRNA compared with $β_1$AR mRNA, and the mRNA abundance of $β_1$AR mRNA determined by ribonuclease protection was 6-10 times that determined by quantitative RT-PCR. Therefore, in the RT-PCR determinations in this study, the calculated amount of $β_1$AR mRNA was multiplied by 7.5.

Three reverse transcriptase reactions were necessary to ensure collinear amplification of the internal standard and cDNAs of interest. Stated another way, it is necessary for the reverse transcribed internal standard and the unknown mRNA to be within 10-fold of one another before amplification in order to obtain collinearity. In general, one reverse transcriptase reaction each was used for low ($\beta$ARs), medium (ANP, $\alpha$-MHC), and high (SRCA, $\beta$-MHC) abundance messages. The precision of the assay as assessed by repeat measurements on the same sample yielded a coefficient of variation of 12.8% for $\beta_1$AR mRNA, and 10-20% for all gene products tested (n=8). All PCR products were confirmed to be the expected cDNA by subcloning the PCR product using the PGEM-T vector system (Promega, Madison, Wis.), and then sequencing the cloned fragment.

The sequences of the MHC primers used in the RT-QPCR assay are presented below. The nucleotide numbering referred to is that used in Kurabayashi et al., *J. Clin. Invest.*, 82, 524-531 (1988).

The 5' primer for $\alpha$-MHC corresponds to nucleotides 1327-1347 of Kurabayashi et al., *J. Clin. Invest.*, 82, 524-531 (1988). Its sequence is:

5'-ATCAAGGAGCTCACCTACCAG-3' SEQ ID NO:1.

The 3' primer for $\alpha$-MHC corresponds to nucleotides 1592-1572. Its sequence is:

3'-CACTCCTCATCGTGCATTTTC-5' SEQ ID NO:2.

SEQ ID NO:2 anneals to a portion of the $\alpha$-MHC cDNA, including the end of the coding sequence, which differs substantially from the sequence of the corresponding portion of the $\beta$-MHC cDNA. See Kurabayashi et al., *J. Clin. Invest.*, 82, 524-531 (1988).

The sequence of the 5' primer for $\beta$-MHC is the same as that of the 5' primer for $\alpha$-MHC:

5'-ATCAAGGAGCTCACCTACCAG-3' SEQ ID NO:1.

The 31 primer for $\beta$-MHC corresponds to nucleotides 1662-1643. Its sequence is:

3'-AGCTGTTACACAGGCTCCAG-5' SEQ ID NO:3.

SEQ ID NO:3 anneals to a portion of the 31 noncoding region of the $\beta$-MHC cDNA which differs substantially from the sequence of the corresponding portion of the $\alpha$-MHC cDNA. See Kurabayashi et al., *J. Clin. Invest.*, 82, 524-531 (1988).

As noted above, the coding region of the synthetic gene contained sequences corresponding to that of the primers used to amplify the $\alpha$-MHC and $\beta$-MHC cDNAs. Thus, the sequence of the $\alpha$-MHC portion of the synthetic gene was:

5'-ATCAAGGAGCTCACCTACCAGGTGAG-
GAGTAGCACGTAAAAG-3'

3'-TAGGGCCGCGAGTGGATGGTCCACTCCT-
CATCGTGCATTTTC-5'

SEQ ID NOS:4 and 5.

The sequence of the $\beta$-MHC portion of the synthetic gene was:

5'-ATCAAGGAGCTCACCTACCAGTCGA-
CAATGTGTCCGAGGTC-3'

3'-TAGGGCCGCGAGTGGATGGTCAGCTGT-
TACACAGGCTCCAG-5'

SEQ ID NOS:6 and 7.

All nucleotides were synthesized by Operon Technologies, Inc. For the sequences of the other primers, see Lowes et al., *J. Clin. Invest.*, 100, 2315-2324 (1997), the complete disclosure of which is incorporated herein by reference.

First-strand cDNA was synthesized from the total RNA using reverse transcriptase (SuperScript II RT, BRL Life Technologies, Inc., Gaithersburg, Md.) and oligo dT (BRL Life Technologies Inc.) from 1 µg of extracted total RNA according to manufacturer's instructions.

The PCR was carried out in a total volume of 100 µl containing 10 mM Tris-HCl, 50 mM KCl, 1.5 mM $MgCl_2$, 0.001% (w/v) gelatin, 160 µM dNTPs, 13 pmol of each primer, and 1.25 units of *Thermus aquaticus* DNA polymrase (Taq polymerase) (Perkin-Elmer/Cetus Corp., Norwalk, Conn.). A trace amount of $^{32}$P-labeled 3' primer was added to provide $3\times10^6$ cpm. The mixture was amplified with a thermal cycling system (TempCycle, Coy Corp., Ann Arbor, Mich.). Each reaction also contained a known quantity of internal standard cDNA prepared by reverse transcription of the synthetic gene. Amplification temperatures were 94° C. for 1.5 minutes for denaturation, 50-55° C. for 1.5 minutes for primer annealing, and 72° C. for 1.5 minutes for primer extension. The primer-annealing temperature varied according to the specific primers being used for amplification.

The amount of DNA synthesized was quantified by measuring the amount of $^{32}$P-end labeled primer incorporated into the PCR products. To do so, 10 µl of each PCR reaction mixture was removed and electrophoresed in an agarose gel. Gels were visualized with ethidium bromide staining and indirect UV irradiation. Bands representing amplification products from the cDNA of interest and the internal standard cDNA were cut out of the gel. Radioactivity in the bands was determined by Cerenkov counting. To ensure that measurements were performed during the exponential phase of amplification, the PCR reaction mixtures were sampled during cycles 15-33 of amplification.

Amplification curves for the internal standard cDNA and the cDNA generated from the mRNA of interest were constructed by plotting the amount of radioactivity in the excised gel bands against the number of PCR cycles. Since a known amount of internal standard cRNA (determined spectrophotometrically) was carried through the cDNA synthesis and amplification, the amount of an mRNA of interest could be determined by extrapolation from the internal standard cDNA standard curve. It is essential that this extrapolation be performed during the exponential phase of amplification and from regions of the amplification curves that are collinear.

Bivariate statistical analyses were performed with Statview 512™ (Brainpower, Inc., Calabasas, Calif.) and multivariate and nonparametric analyses were performed with SAS (SAS Institute, Cary, N.C.). Unless otherwise specified, data are expressed as mean ± standard error. The two-sided significance level was P<0.05. Three-group comparisons were performed with ANOVA for continuous variables and by contingency table analysis for binary variables. With a significant three-group comparison, specific two-group comparisons were performed with the Scheffe or Bonferroni multiple comparisons procedures. When data were not normally distributed as assessed by the Shapiro-Wilk test, the ANOVA and t test results were confirmed by the Kruskal-Wallis and Wilcoxon tests, respectively. Univariate and multivariate relationships between continuous variables were assessed with stepwise linear regression, using P=0.15 to enter and to remove.

The results are presented in Table 2. As can be seen, compared with the nonfailing groups, $\beta_1$AR mRNA abundance is reduced in both the PPH and IDC groups (by ~50% in the IDC group and 60% in the PPH group). Surprisingly, the PPH group exhibited an increase in $\beta_2$AR mRNA abundance of 85% compared with the nonfailing group and of 152% compared with the IDC group. The data for ANP are consistent with an increase in ANP gene expression in both the PPH and IDC groups. There were no differences in expression of SRCA mRNA among the three groups.

The RV endomyocardium of the nonfailing hearts contained a substantial amount of the α isoform of MHC (~37.0× $10^5$ molecules/μg total RNA, range 10.7-72.2). However, β-MHC is the dominant isoform in all three groups. Both PPH and IDC exhibited a marked decrease in α-MHC mRNA abundance (by 75% in PPH and 60% in IDC). As can be seen, compared with the nonfailing group there is a tendency for the abundance of β-MHC to be slightly higher in both PPH and IDC groups (P=0.06 by ANOVA). The percentage of total MHC represented by the α-MHC isoform decreased from 23.1 to 5.6% in PPH and to 7.6% in IDC (both P<0.001). The change in the percentage of β-MHC varied from 76.9% in nonfailing ventricles to 94.4% in PPH and 92.2% in IDC. The MHC data are surprising because an MHC isoform shift was not thought to occur in failing human hearts (see Background section).

The data in Table 2 confirm previous findings of a down-regulation of $β_1AR$ mRNA in the failing human left ventricle (LV) (Bristow et al., *J. Clin. Invest.*, 92, 2737-2745 (1993)) and in endomyocardial biopsies taken from failing RVs (Englehardt, et al., *J. Am. Coll. Cardiol.*, 27, 146-154 (1996)). The data also confirm previous reports of an up-regulation of ANP (LV free wall as starting material) (Feldman et al., *Circulation*, 83, 1866-1872 (1991)). The results do not confirm previous data from end-stage IDC explanted hearts showing that SRCA mRNA is down-regulated (Mercadier et al., *J. Clin. Invest.*, 85, 305-309 (1990)), but are in agreement with some investigators' measurements of SRCA protein mass (Movsesian et al., *Circulation*, 90, 653-657 (1994)) and activity (Movsesian et al., *Circ. Res.*, 65, 1141-1144 (1994)) in end-stage, explanted human hearts.

Finally, recent experiments (data not shown) demonstrate that the amounts of α-MHC and β-MHC mRNA and changes in the mRNA levels correlate with the amounts and changes in α-MHC and β-MHC protein measured in the same tissue samples. These results confirm the results of others who have also found that MHC mRNA and protein levels are closely correlated (Nadal-Ginard et al., *J. Clin. Invest.*, 84, 1693-1700 (1989)).

Example 2

Measurement of MHC Isoforms in Three Different Regions of Human Ventricular Myocardium The amount of mRNA coding for α-MHC, β-MHC, $β_1AR$, $β_2AR$, SRCA and ANP in total mRNA extracted from different areas of human hearts was measured as described in Example 1. The specimens were taken from the RV endomyocardium ("RV endo"), from full thickness mid RV free wall (RV FW), and from full thickness mid LV free wall (LV FW). The RV endo samples were taken by simulated endomyocardial biopsies. The hearts were taken from 6 patients with end-stage biventricular failure (LVEF=14±2%) from idiopathic dilated cardiomyopathy (IDC) prior to transplantation (age 45±5 years) and from 6 prospective organ donors (NF) (age 38±7 years). The hearts of the prospective organ donors were ultimately rejected for transplantation for non-cardiac reasons, but they had no history of cardiac disease and had normal cardiac function by medical history and echocardiograph or inspection at the time of organ harvest (LVEF≧45%).

The results are presented in Table 3 below (mRNA molecules×$10^5$/μg total RNA±SEM). As can be observed, α-MHC expression is significantly decreased in all three types of tissue from IDC hearts, as compared to NF hearts. The β-MHC expression is increased in all three types of tissue and is significantly increased in RVFW and LVFW, as compared to NF hearts. Also, there is good agreement between absolute levels of mRNA coding for α-MHC, β-MHC, $β_1AR$, $β_2AR$, and ANP in the three sampled regions. Levels of SRCA mRNA appear to be slightly lower in the LVFW as compared to either RV location. Note also that the data are in agreement with the changes in mRNA levels detected in endomyocardial biopsy tissue from in vivo sampled hearts (see Table 2 above).

Similar changes in expression of α-MHC and β-MHC in IDC are observed in all three regions. Gene expression in RV endomyocardium is, therefore, representative of gene expres-

TABLE 1

| Group | RVEF (%) | LVEF (%) | RA (mmHg) | PAP (mmHg) | PW (mmHg) | Cardiac Index (L/min/m²) |
|---|---|---|---|---|---|---|
| NF (n = 8) | 52 ± 2 | 59 ± 3 | 2.5 ± 1.9 | 14.8 ± 3.5 | 5.0 ± 1.9 | 4.46 ± 0.46 |
| PPH (n = 7) | *29 ± 2 | 53 ± 3 | 9.1 ± 2.3 | *49.6 ± 4.8 | 6.1 ± 1.2 | *2.06 ± 0.18 |
| IDC (n = 29) | 33 ± 3 | *@23 ± 1 | 6.7 ± 1.1 | @27.9 ± 1.9 | @15.0 ± 1.6 | *2.49 ± 0.14 |

*p < .05 vs. NF by ANOVA/Scheffe Test
p < .05 vs. IDC by ANOVA/Scheffe Test
@p < .05 vs. PPH by ANOVA/Scheffe Test

TABLE 2

| Source of RNA (number)@ | mRNA abundance, molecules × $10^5$/μg total RNA (±SEM) | | | | | | MHC isoform % | |
|---|---|---|---|---|---|---|---|---|
| | $β_1AR$ | $β_2AR$ | ANP | SRCA | α-MHC | β-MHC | % α-MHC | % β-MHC |
| IDC (n = 29) | *1.6 ± 0.4 | 1.9 ± 0.1 | *108 ± 20 | 76.0 ± 5.0 | *14.8 ± 1.8 | 183 ± 14 | *7.6 ± 1.1 | *92.2 ± 1.0 |
| PPH (n = 7) | *1.2 ± 0.1 | #*4.8 ± 1.1 | *140 ± 45 | 75.0 ± 4.6 | *9.2 ± 1.8 | 183 ± 28 | *5.6 ± 2.0 | *94.4 ± 2.0 |
| NF (n = 8) | 3.1 ± 0.8 | 2.7 ± 0.6 | 35.0 ± 12.9 | 80.3 ± 13.0 | 37.0 ± 6.5 | 108 ± 15 | 23.1 ± 0.8 | 76.9 ± 0.8 |

*p < .05 vs. NF (ANOVA)
p < .05 vs. IDC (ANOVA)
@The average age, in years, of the tissue donors was:
IDC 55.0 ± 2.0 (p < 0.05 vs PPH by ANOVA);
PPH 36.6 ± 2.8 (p < 0.05 vs. IDC by ANOVA); and
NF  49.1 ± 4.6.

sion in the more functionally relevant RV free wall and can be used to assess RV function generally. Further, these results also show that gene expression in RV endomyocarium can be used to assess LV function, when LV and RV function are equally affected, as in the IDC subjects.

onds×2, IKA-Works, Cincinnati, Ohio). After centrifugation (12,000 g for 15 minutes), the aqueous phase was collected, and RNA was precipitated by the addition of the same volume of isopropanol. Then, the RNA pellet was washed with 70% ethanol and resuspended in water treated with diethyl pyro-

TABLE 3

| Region | $\beta_1$-AR | | $\beta_2$-AR | | ANP | | SRCA | | $\alpha$-MHC | | $\beta$-MHC | |
|---|---|---|---|---|---|---|---|---|---|---|---|---|
| | NF | IDC | NF | IDC | NF | IDC | NF | IDC | NF | IDC | NF | IDC |
| RV endo | 4.9 ± .4 | *3.1 ± .3 | 2.5 ± .3 | 2.0 ± .3 | 34 ± 2 | *121 ± 26 | 86 ± 5 | 75 ± 9 | 46 ± 7 | *9.4 ± 1.1 | 111 ± 7 | 142 ± 5 |
| RV FW | 4.7 ± .4 | *3.3 ± .4 | 2.1 ± .5 | 1.8 ± .3 | 32 ± 2 | *92 ± 18 | 101 ± 12 | 79 ± 10 | 54 ± 6 | *9.7 ± 1.6 | 104 ± 11 | *163 ± 6 |
| LV FW | 4.8 ± .6 | *2.9 ± .6 | 2.1 ± .4 | 1.6 ± .2 | 38 ± 5 | *110 ± 24 | $^\delta$68 ± 9 | $^\delta$56 ± 6 | 46 ± 9 | *8.9 ± 1.9 | 118 ± 10 | *146 ± 18 |

*p < .05 vs. NF
p < .10 vs. NF
$^\delta$p < .10 vs. RV endo or RV FW (ANOVA)

Example 3

Measurement of MHC Isoforms in Human Left Ventricles

The amount of mRNA coding for $\alpha$-MHC and $\beta$-MHC in total mRNA extracted from left ventricles (LVs) was measured. The hearts were taken from 14 prospective organ donors (age 34.4±±13.9 years) and from 19 patients undergoing cardiac transplantation for chronic end-stage heart failure (age 50.1±14.6 years).

The 14 prospective organ donors (control subjects) were motor vehicle accident victims, cerebral vascular accidents, and suicides by gunshot. They had no cardiac history and no significant structural abnormalities on cardiac donor screening using echocardiography and, in subjects >50 yr of age, coronary angiography. All control subjects were maintained under intensive care, but seven of the hearts (NF) were excluded ultimately from heart donation because of age, body size, or blood type incompatibility. In all NF heart cases, the echocardiogram revealed normal LV systolic function. The remaining 7 of the 14 control subjects were identified as having acute donor heart dysfunction (DHD), which is thought to be due to myocardial injury from massively increased sympathetic output accompanying brain injury. These hearts were excluded from heart donation because of decreased LV systolic function (ejection fraction≦45%). In all DHD cases, the echocardiogram revealed diffuse hypokinesis without segmental LV wall motion abnormalities.

The 19 heart failure patients had the following diagnoses: idiopathic dilated cardiomyopathy (IDC) (6), valvular cardiomyopathy (VHD) (2), end-stage hypertrophic cardiomyopathy (1), orthotopic heart transplantation (1), or ischemic cardiomyopathy (IHD) with history of coronary artery disease and at least one myocardial infarction (9).

The hearts were placed in ice-cold oxygenated saline immediately after removal, and myocardial specimens were gathered within 10 minutes after explantation. A transmural specimen was taken from the medial part of the left ventricular free wall when possible, and midway between the apex and base, at least 2 cm away from the scar in patients with myocardial infarction. Immediately after sampling, myocardial specimens were frozen in liquid nitrogen and stored at −80° C. until used.

Total RNA was isolated from 35-276 mg of frozen left ventricular myocardium specimen using a modification of the acid guanidinium thiocyanate-phenol-chloroform method. Chomczynski and Sacchi, *Anal. Biochem.*, 162, 156-159 (1987). Briefly, the frozen tissue was homogenized at 4° C. in 2.0 ml of RNA STAT-60 (Tel-Test "B", TelTest, Inc., Friendswood, Tex.) with an Ultra-Turrax (13,500 rpm for 30 seconds×2, IKA-Works, Cincinnati, Ohio). After centrifugation (12,000 g for 15 minutes), the aqueous phase was collected, and RNA was precipitated by the addition of the same volume of isopropanol. Then, the RNA pellet was washed with 70% ethanol and resuspended in water treated with diethyl pyrocarbonate to inactivate ribonucleases. The concentration of extracted total RNA was determined using a spectrophotometer (Hitachi U-2000, Hitachi Sci. Instrs., Mountain View, Calif.).

First-strand cDNA was synthesized from the total RNA using reverse transcriptase (SuperScript II RT, GIBCO BRL, Gaithersburg, Md.) and random hexamer (GIBCO BRL) from 2 μg of extracted total RNA according to manufacturer's instructions.

Two primers were designed from reported $\alpha$-MHC and $\beta$-MHC cDNA sequences and were synthesized by GIBCO BRL. The sequences of these primers were:

5' primer—5'-AGCAGAAGCGCAACGCAGAGT-3' SEQ ID NO: 8

3' primer—3'-GTTCAAGGCGTTCCACGTCGT-5' SEQ ID NO:9.

These primers are identical in sequence between $\alpha$-MHC and $\beta$-MHC, and the amplified 217-bp sequence was 96% identical between $\alpha$-MHC and $\beta$-MHC. The $\alpha$-MHC and $\beta$-MHC cDNAs were, therefore, amplified with equal efficiency. The 5' primer is located in exon 36 and 37 of the $\alpha$-MHC and $\beta$-MHC genes, respectively. The 3' primer is located in exon 38 and 39 of the $\alpha$-MHC and $\beta$-MHC genes, respectively. The two exon/intron boundaries are conserved. The amplified regions correspond to nucleotides 5492-5708 and 5572-5788 in $\alpha$-MHC and $\beta$-MyHC cDNA, respectively. Matsuoka et al., *Am. J. Med. Genet.*, 41, 537-547 (1991); Jaenicke et al., *Genomics*, 8, 194-206 (1990).

The PCR was carried out in a total volume of 50 μl containing 10 mM Tris-HCl, 50 mM KCl, 1.5 mM MgCl$_2$, 0.2 mM dNTPs, 15 pmole of each primer, and 2.5 units of *Thermus aquaricus* DNA polymerase (Taq polymerase) (Perkin-Elmer/Cetus Corp, Norwalk, Conn.). The mixture was amplified with a thermal cycling system (OmniGene Hybaid Ltd., Middlesex, UK) with the following conditions. After the "hot start" at 94° C. for 3 minutes, amplification was done by 21 cycles of the following program: 94° C. for 45 seconds for denaturation, 55° C. for 45 seconds for annealing, and 72° C. for 90 seconds for primer extension. Then, the mixture was kept at 72° C. for 10 minutes and held at 30° C.

The amplified 217-bp fragment was digested with endonucleases, PstI or SacI (New England BioLabs, Inc., Beverly, Mass.). Only the $\beta$-MHC product has PstI sites, while both MHC products have SacI sites. Therefore, the 217-bp bands remaining after digestion with PstI or SacI correspond to the amplified $\alpha$-MHC cDNA and the background, respectively.

When SacI digestion did not completely eliminate the background (a very rare occurrence), the assay was not considered valid and was re-run. Digestion was performed in a total volume of 20 μl containing 5 μl of PCR product, with appropriate buffers, with (PstI, 20 units, or SacI, 20 units) or without (replaced by distilled water) restriction enzymes, at 37° C. for 3 hours according to the manufacturer's instructions.

The digested fragments were subjected to 8% polyacrylamide gel electrophoresis (8 μl of 20 μl reaction, room temperature, 10V/cm constant) with a Mighty Small II (Hoefer Pharmacia Biotech, Inc., San Francisco, Calif.). The gel was stained with CYBR Green I (diluted 1:10,000, Molecular Probes, Inc., Eugene, Oreg.) for 60 minutes with gentle agitation. CYBR Green I is an intercalating fluorescent dye that binds specifically to nucleic acids. The digested fragments were clearly separated from the original 217-bp band. The fluorescence signal of the 217-bp bands was detected using a fluorescence imaging system (STORM, Molecular Dynamics, Sunnyvale, Calif.) and the intensity was evaluated with a quantification program (ImageQuant, Molecular Dynamics, CA). The relative amount of amplified α-MHC cDNA to total MHC (α-MHC+β-MHC) was expressed as follows:

Amplified α-MHC cDNA ratio(%)=$100[SI_{PstI}-SI_{SacI}]/[SI_{Enz-}-SI_{SacI}]$, where $SI_{PstI}$, $SI_{SacI}$ and $SI_{Enz-}$ are the signal intensity (in arbitrary units) of the 217-bp band after incubation with PstI, with SacI, or without endonucleases, respectively.

The results are presented in Table 4 below. Note that the NF group had a measurable amount of the fast contracting α-MHC isoform, consistent with the measurements made in RV endomyocardial biopsy material (Example 1). The DHD group also had a measurable amount of α-MHC. Failing human LVs exhibited a significant reduction in α-MHC as compared to NF controls. MHC mRNA and protein levels are closely correlated (see Nadal-Grinard et al., *J. Clin. Invest.*, 84, 1693-1700 (1989) and Example 1), and these differences in gene expression should be reflected in the amount of α-MHC protein.

Assuming a 4-fold difference in speed of contraction in favor of the α-isoform, these changes would result in a 44-46% reduction in velocity of shortening in the failing group. The mean values of total MHC cDNA were not statistically different among all three patient groups: NF—827±215, DHD—1062±570, and F—951±449 (arbitrary units).

TABLE 4

| Group | LVEF (% ±SEM) | α-MHC mRNA (% ±SEM) |
| --- | --- | --- |
| NF (n = 7) | 63 ± 5 | 33.3 ± 18.9 |
| DHD (n = 7) | $29 ± 11 | @35.4 ± 16.5 |
| F (n = 19) | $18 ± 6 | *2.2 ± 3.5 |

NF = nonfailing
DHD = donor heart dysfunction
F = all heart failure patients
*p < .05 vs. NF and DHD (ANOVA)
@p < 0.05 us F (ANOVA)
$p < 0.05 us NF (ANOVA)

The data are expressed as mean ± standard deviation. The data were analyzed by the nonparametric analogues of ANOVA and the two-tailed t test, which are the Kruskal-Wallis and the Wilcoxon rank-sum test, respectively. By Kruskal-Wallis, P=0.0001. By Wilcoxon, for comparisons of NF vs. DHD, NF vs. F, and DHD vs. F hearts, P values were 1.000, 0.0001, and 0.0001, respectively.

The accuracy of the RT-PCR was verified by performing a ribonuclease protection assay (RPA) using the same specimens. The RPA was performed as described in Nakao et al., *J. Clin. Invest.*, 100, 2362-2370 (1997), the complete disclosure of which is incorporated herein by reference. The α-MHC ratios obtained by RPA were in good agreement with those obtained by RT-PCR ($r^2$=0.93).

Example 4

Decrease in α-MHC and Increase in β-MHC Gene Expression with Aging

The amount of mRNA coding for α-MHC and β-MHC in total mRNA extracted from LVs was measured. The LVs were taken from the hearts of 22 prospective organ donors of varying ages. The organ donors were ultimately rejected for transplantation for non-cardiac reasons, but they had no history of cardiac disease and had normal cardiac function by medical history and echocardiograph or inspection at the time of organ harvest. All procedures were as described in Example 3.

The results are shown in Table 5 below. A significant reduction in percent α-MHC with age was found (r value=0.53, p<0.05). In Table 5, older patients were >40 years old.

TABLE 5

| Age Group (n) | Age (years) | α-MHC (%) | β-MHC (%) |
| --- | --- | --- | --- |
| Younger (n = 12) | 25.8 ± 2.3 | 38.2 ± 5.8 | 61.8 ± 5.8 |
| Older (n = 10) | *53.8 ± 2.0 | *19.4 ± 5.6 | *80.6 ± 5.6 |

*p < 0.05 versus younger

Example 5

Up-Regulation of α-MHC and Down-Regulation of β-MHC by Medical Treatment

The amount of mRNA coding for α-MHC, β-MHC, $β_1$AR, $β_2$AR, SRCA, and ANP in total mRNA extracted from endomyocardial biopsies was measured as described in Example 1. The tissues were taken from 29 human subjects diagnosed with idiopathic dilated cardiomyopathy who had completed six months of treatment with either β-adrenergic blockade, a medical treatment which can improve systolic function, or placebo. The β-blocking agents used were either carvedilol or metoprolol.

The results are given in Table 6 below. The subjects are divided into those who experienced improvement in LV function (EF increased by >5 units) versus those who did not (EF showed no significant change or decreased). All subjects improving (n=15) were on β-blockade. Eleven of the 14 subjects not improving were on placebo, and three were on β-blockade. In the subjects showing improved ventricular function, the average LVEF improved from 21-41% and the average RVEF improved from 30-40%. As can be observed from Table 6, the only statistically significant changes exclusively associated with improved left ventricular function are an increase in the amount of α-MHC mRNA and a decrease in the amount β-MHC.

TABLE 6

| Category | ΔLVEF Response | Δβ$_1$AR | Δβ$_2$AR | ΔANP | ΔSRCA | Δα-MHC | Δβ-MHC |
|---|---|---|---|---|---|---|---|
| | | (molecules mRNA × 10$^5$/μg total RNA ± SEM) | | | | | |
| Improved (n = 15) | +18.5 ± 2.2*# | −0.17 ± 0.32 | +0.22 ± 0.18 | −36.6 ± 14.2 | +5.7 ± 5.1 | +6.8 ± 3.7*$ | −16.4 ± 20.6* |
| Not Improved (n = 14) | −1.4 ± 1.2 | −0.25 ± 0.38 | +0.21 ± 0.75 | −36.4 ± 19$ | +1.8 ± 7.0 | −3.8 ± 1.5# | +54.8 ± 26.1$ |

*$p < 0.05$ versus not improved.
$p < 0.05$ versus baseline
$$p < 0.10$ versus baseline

Example 6

Effect of Thyroid Hormone on Human Hearts

Contractile responses of isolated right ventricular (RV) trabeculae harvested from transplant recipients with end-stage heart failure (failing) were measured as previously described in Bristow et al., *Circ. Res.*, 59, 297-309 (1986). Briefly, isolated RV trabeculae of uniform size (2 mm×8 mm) were mounted in an eight-chamber muscle bath containing Tyrode's solution bubbled with 95% $O_2$-5% $CO_2$ and paced at 1.0 Hz at 10% above the threshold for initiating contraction. Resting tension placed on the trabeculae was set at the length that produced the maximum degree of systolic contraction, usually ≈1 gram tension. Tissues were assigned to a treatment group and incubated for 4 or 12 hours with 1 nM triiodothyronine (T3) or vehicle (as control), with bath changes every 30 minutes. At the end of the incubation period, full dose-response curves to isoproterenol were performed using 0.5 log unit dose increments between $10^{-9}$ and $10^{-4}$M. After completion of the isoproterenol dose-response curve and wash-out of isoproterenol, the maximal response to calcium was measured by administering calcium chloride at final concentrations of 2.5, 5, and 10 mM. Tension was recorded as the stimulated tension minus baseline tension, and the maximum response was taken as the greatest amount of net tension produced at any point in the dose-response curve. Finally, after the contractility measurements were completed, the α-MHC, β-MHC, β-AR, and SRCA gene expression in the trabeculae were measured by quantitative RT-PCR as described in Example 1.

The results of the isoproterenol contractility measurements are presented in FIGS. 1A (4-hour incubation) and 1B (12-hour incubation). The α-MHC and β-MHC gene expression measurements are presented in Table 7 below. There were no significant differences in adrenergic receptor or SRCA gene expression in the T3 group as compared to the control group.

TABLE 7

Percentage of α- and β-MHC isoform mRNA present at baseline and following incubation with and without T3

| | % α-MHC | % β-MHC |
|---|---|---|
| Baseline | 10.7 ± 3.19 | 89.3 ± 3.19 |
| +T3 incubation | 24.5 ± 9.29* | 75.5 ± 9.29* |
| −T3 incubation | 14.6 ± 6.67 | 85.4 ± 6.66 |

*$p < .05$ vs. no T3

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

We claim:

1. A method of treating myocardial failure in a human comprising administering an effective amount of a transgene encoding for α-MHC, wherein expression of α-MHC provides improvement in left ventricular ejection fraction.

* * * * *